United States Patent [19]
Lamb

[11] Patent Number: 5,010,880
[45] Date of Patent: Apr. 30, 1991

[54] HOME TRACTION DEVICE

[76] Inventor: Mark A. Lamb, 2535 S. Black Cat Rd., Meridian, Id. 83642

[21] Appl. No.: 350,456

[22] Filed: May 11, 1989

[51] Int. Cl.⁵ .......... A61F 5/00
[52] U.S. Cl. .......... 128/71; 128/70
[58] Field of Search .......... 128/24.1, 33, 84 R, 128/69, 70, 71, 128

[56] References Cited

U.S. PATENT DOCUMENTS

| | | | |
|---|---|---|---|
| Re. 24,487 | 6/1958 | Leach | 128/33 |
| 263,625 | 8/1882 | Taylor | 128/70 |
| 1,126,460 | 1/1915 | Hawley | 128/71 |
| 1,234,536 | 7/1917 | Goldman | 128/71 |
| 1,280,987 | 10/1918 | Gregory | 128/71 |
| 1,374,115 | 4/1921 | Roemer | 128/71 |
| 1,642,158 | 9/1927 | Kubista | 128/71 |
| 1,936,363 | 11/1933 | Murray | 128/71 X |
| 2,584,412 | 2/1952 | Anderson | 128/84 R |
| 2,865,367 | 12/1958 | Sorenson | 128/71 |
| 2,943,620 | 7/1960 | Sibert | 128/24.1 |
| 3,060,925 | 10/1962 | Honsaker et al. | 128/70 X |
| 3,194,232 | 7/1965 | Rickenbach | 128/71 |
| 3,904,195 | 9/1975 | Chavanne | 128/70 X |
| 4,157,088 | 6/1979 | Gracey | 128/70 X |
| 4,356,816 | 11/1982 | Granberg | 128/71 |
| 4,474,370 | 10/1984 | Oman | 128/69 X |
| 4,489,713 | 12/1984 | Latenser | 128/71 |
| 4,508,109 | 4/1985 | Saunders | 128/69 X |
| 4,531,514 | 7/1985 | McDonald et al. | 128/69 X |
| 4,627,423 | 12/1986 | Kampner | 128/71 X |
| 4,664,101 | 5/1987 | Granberg | 128/84 R |
| 4,674,484 | 6/1987 | Kott | 128/69 X |

FOREIGN PATENT DOCUMENTS

| | | | |
|---|---|---|---|
| 0008248 | 2/1980 | European Pat. Off. | 128/69 |
| 152892 | 8/1903 | Fed. Rep. of Germany | 128/84 R |
| 8016554 | 7/1980 | France | 128/71 |

*Primary Examiner*—Richard J. Apley
*Assistant Examiner*—Linda C. Maas Dvorak
*Attorney, Agent, or Firm*—Frank J. Dykas; Craig M. Korfanta

[57] ABSTRACT

A home traction table 10 having a generally planar table 11 being supported by a pair of T-shaped leg members 20 and 21. A pelvic support frame 48 is disposed perpendicular to the plane of the table. A pelvic harness 42 is provided for supporting the pelvic area of patient 1 by attaching harness 42 to pelvic frame 48.

A weight brace 31 is attached to the head end of planar table 11 and extends angularly upward from that end. A pulley 32 is rotatably mounted in the extended end of weight brace 31. A head harness 35 is provided which longitudinally supports the head of patient 1 and is attached by a flexible member, such as rope, to an adjustable weight. The flexible member is slidably received by pulley 32 which converts the downward weight force to a longitudianl tensive traction force.

An elongated rectangular vibrating pad 14 is privotally mounted within planar table 11 and has a vibrator motor 29 attached thereto.

6 Claims, 8 Drawing Sheets

35

HOME TRACTION DEVICE

BACKGROUND OF THE INVENTION

1. Technical Field.

This invention generally relates to traction devices and in particular to a traction device particularly well suited for home use, which is safe and can easily be adjusted without the aid of additional personnel.

2. Background Art.

While many various traction tables are known within the art, almost all are designed for use in a therapy clinic where the various parameters are adjusted by a second person.

Typical of these types of traction tables is that which is taught by DRAUX, U.S. Pat. No. 3,638,646. Draux teaches a therapeutic table having a frame with three slidably mounted platforms thereon. Draux also teaches a footrest which is slidably attached to the frame and an axial vibration device. In use, the patient's ankles are secured to the footrest and the table is inclined so that the patient's feet are higher than his head. Because the platforms slide, the weight of the patient puts his spine under tension. The axial vibrator then induces rapid intermittent traction to the spine of the patient. The device of Draux is not convenient for home use in that it is quite cumbersome and it requires a second person to make the necessary adjustments when the patient is installed on the table. Additionally, the axial vibration taught by Draux does not induce relaxation of muscle spasms, which are the most common cause of lower back pain.

LIND, U.S. Pat. No. 4,002,165 teaches an auto traction table wherein traction is applied by the user with his or her own muscle power. In basic terms, Lind's auto traction table uses a pelvic harness which is fastened to supports at one end of the table to longitudinally support the pelvic area of a user. The user then grabs vertical supports at the other end of the table and pulls against them to put his or her spine under tension. While the Lind device does offer the advantage of having user adjustable tension, it requires the user to exert a substantial amount of energy which is not always practical. Additionally, Lind does not teach the use of any vibration means to induce relaxation.

What is needed is a traction table which includes a relaxation vibrator and which is suitable for home use. The objects of the present invention therefore include, providing a home traction table which is compact in design, easy to use and does not require additional personnel, and further providing a traction table which includes a soothing vibrator to induce muscle relaxation in the spine area.

DISCLOSURE OF INVENTION

These and other objects are accomplished by a generally planar table being supported by a pair of T-shaped supports. The planar table is advantageously disposed at a slight decline from its head to its foot. A pelvic support frame is disposed generally perpendicular to the plane of the table at a point approximately one-third of the distance up the table from its foot end. A pelvic harness is provided for supporting the pelvic area of the patient by attaching the harness to the pelvic frame. A clamcleat is attached to the top pelvic frame member for adjustably attaching the pelvic harness thereto.

A weight brace is attached to the head end of the planar table and extends angularly upward from that end. A pulley is rotatably mounted in the extended end of the weight brace. A head harness is provided which longitudinally supports the head of the patient and is attached by a flexible member such, as a rope, to an adjustable weight. The flexible member is slidably received by the pulley which converts the downward weight force to a longitudinal tensive traction force.

An elongated rectangular vibrating pad is pivotally mounted within the planar table and has a vibrator motor attached thereto. The vibrating pad induces vibrations which are generally normal to the planar surface of the table. These vibrations greatly enhance muscle spasm relaxation in the spinal area. The vibrating pad is therefore disposed within the planar table to coincide with the spine of the patient.

FIG. *2a* is an exploded assembly view of the home traction device.

FIG. *2b* is a detailed view of the clamcleat.

Figure 1:
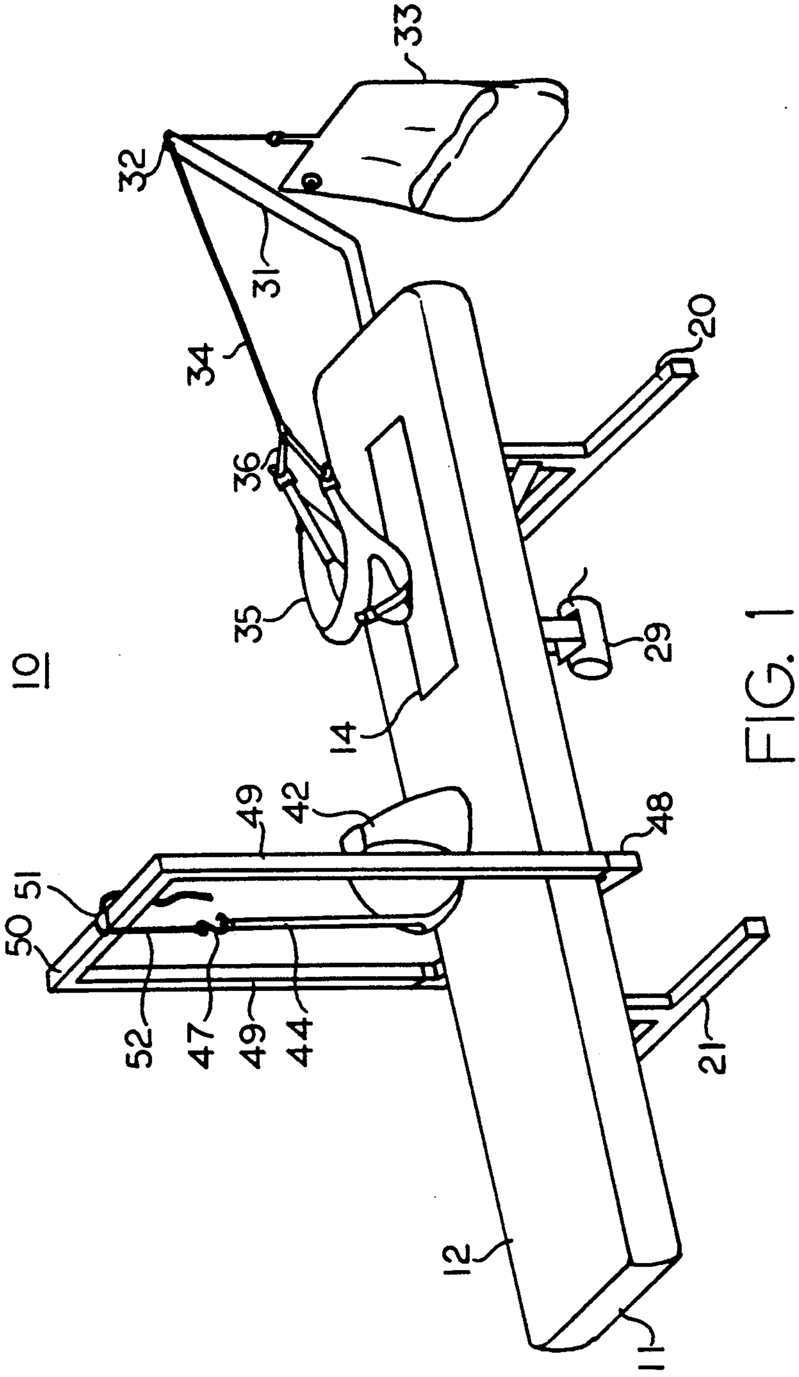
FIG. 1 is a representational elevation view of a home traction device.
Figure 2A:
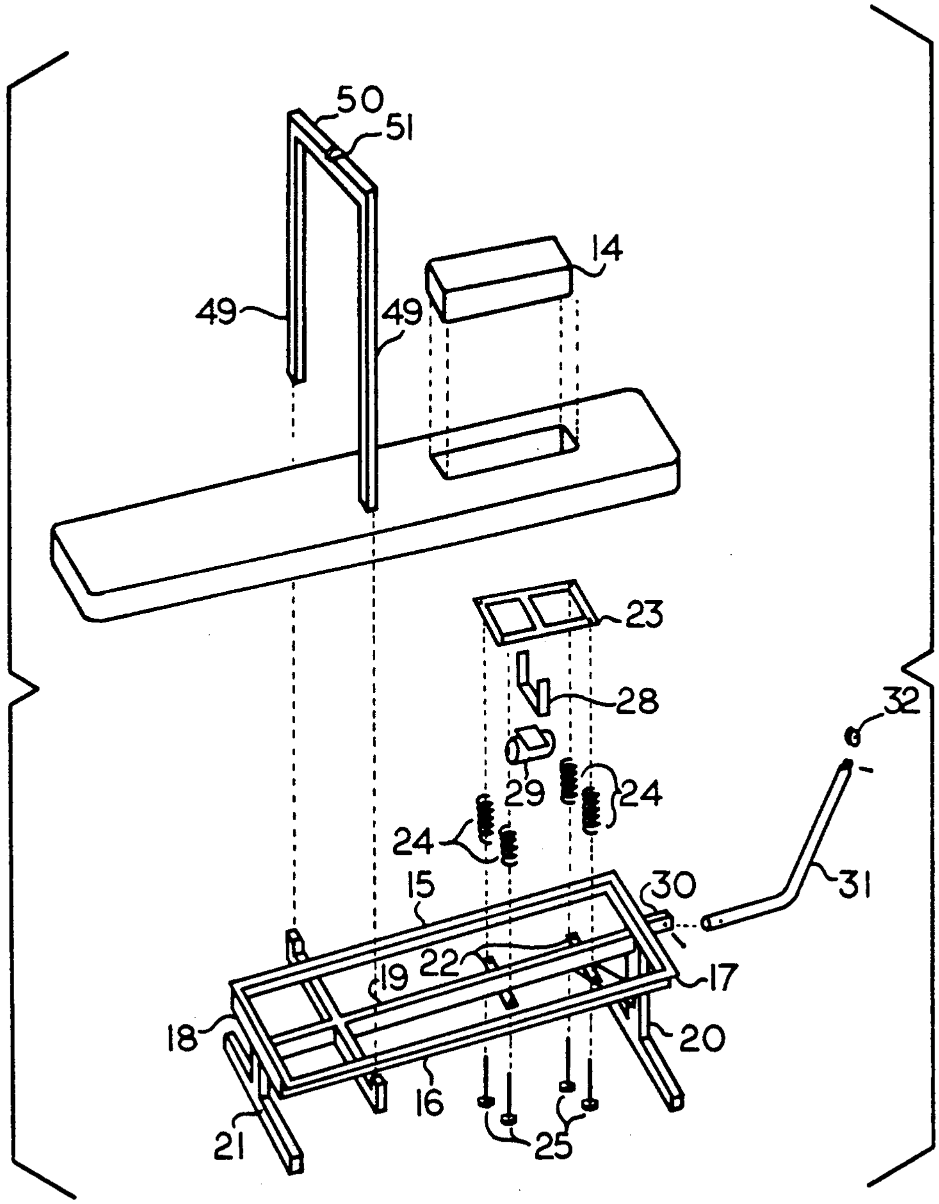
Figure 2B:
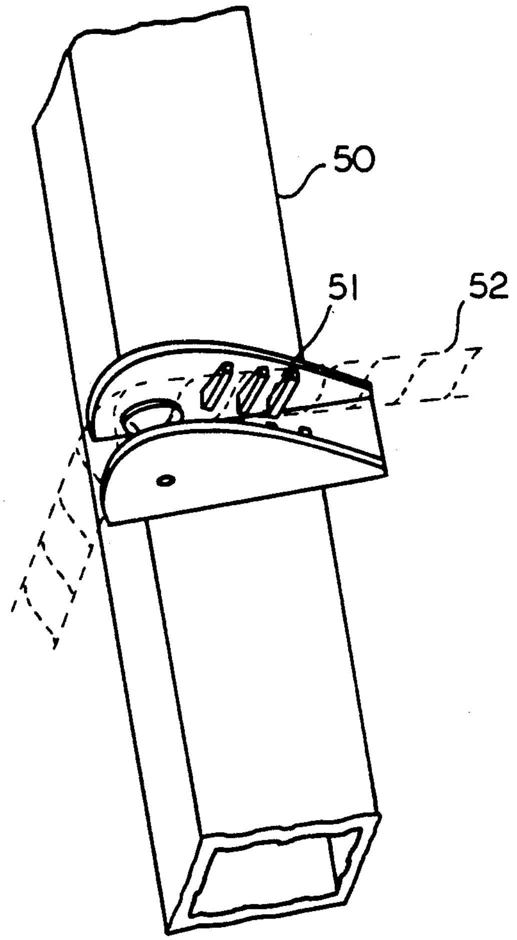
Figure 3:
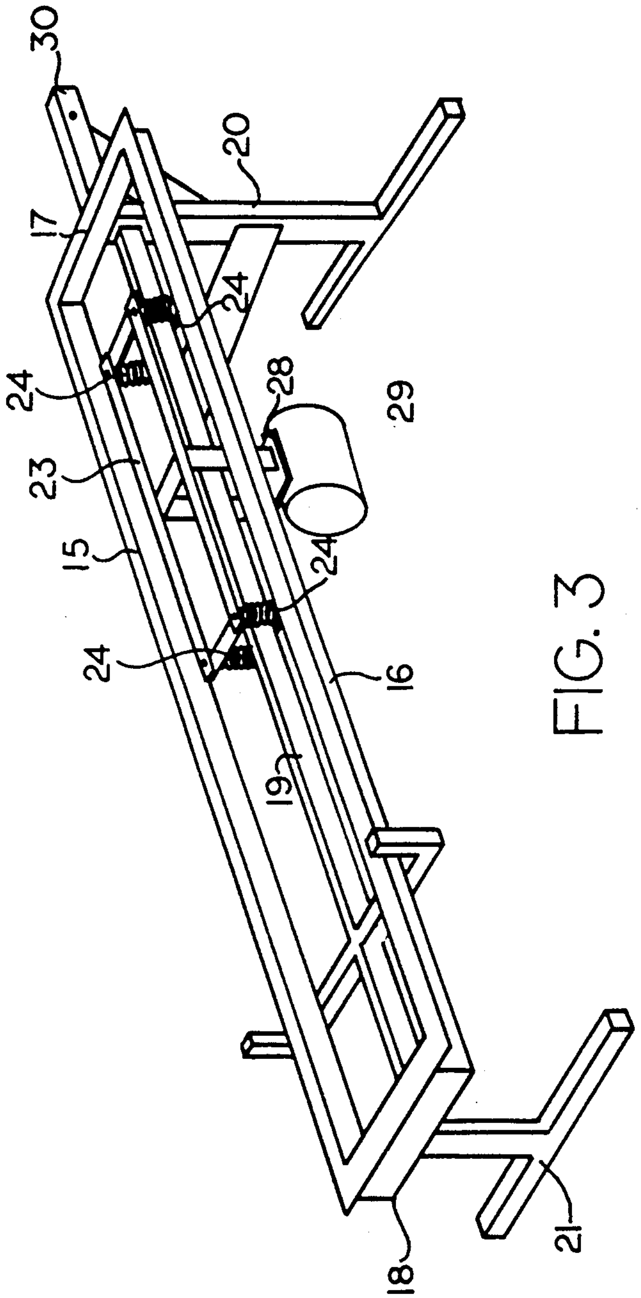

FIG. 3 is a representational view of the traction device frame assembly.

Figure 4:
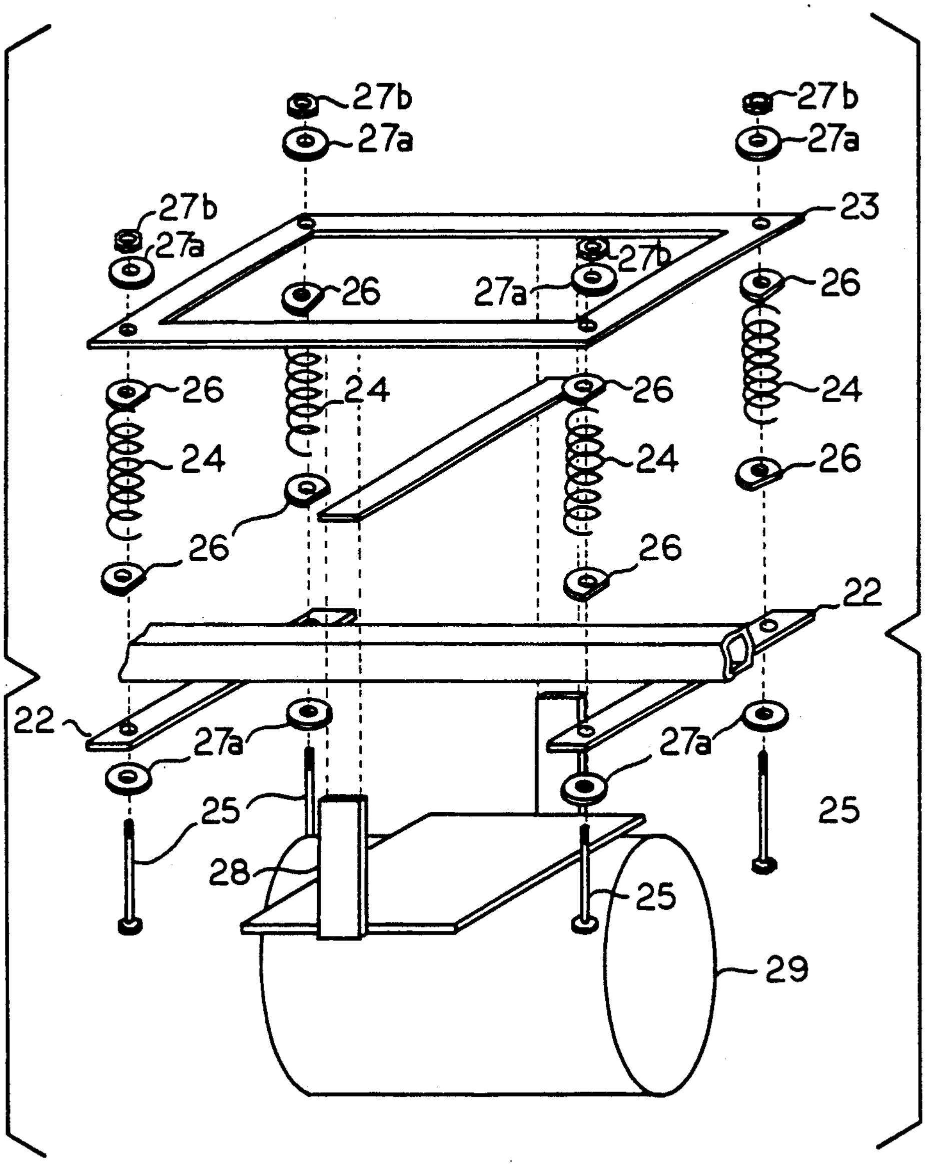

FIG. 4 is a detailed view of the vibrator frame and motor.

Figure 5:
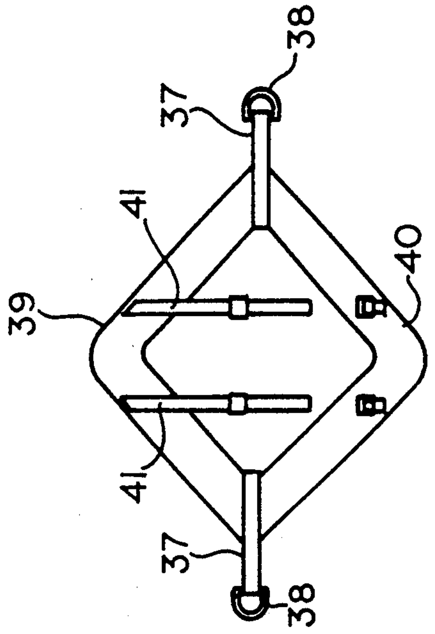

FIG. 5 is a plan view of the head harness.

Figure 6:
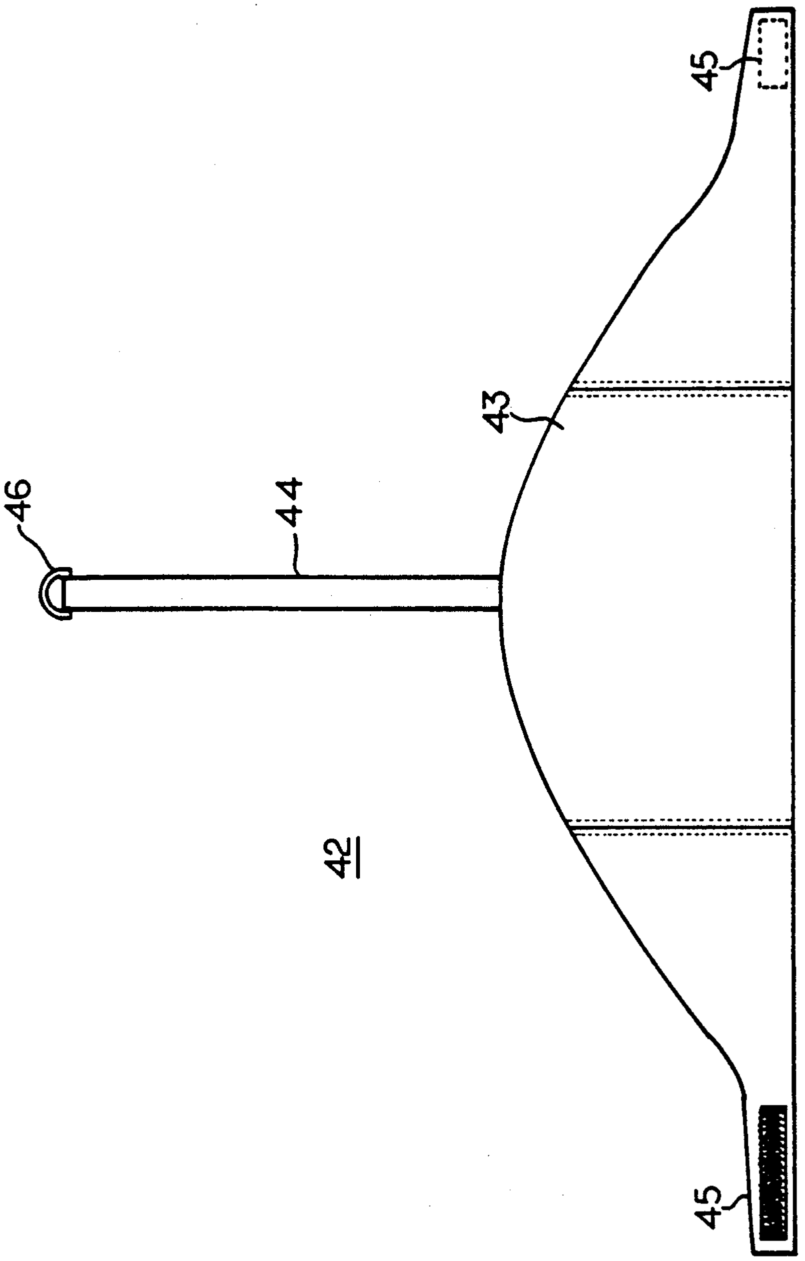

FIG. 6 is a plan view of the pelvic harness.

Figure 7:
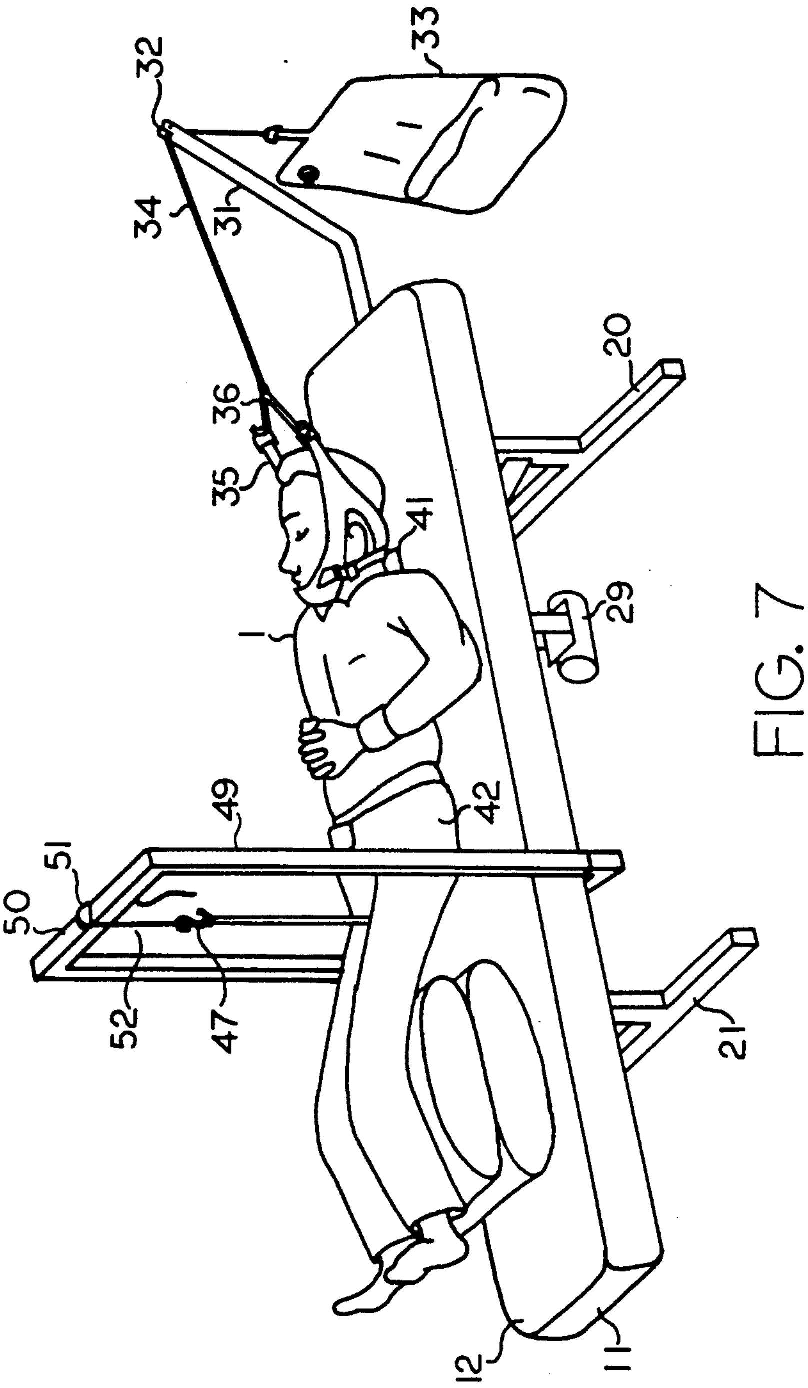

FIG. 7 is a representational elevation view of the home traction device in use.

BEST MODE FOR CARRYING OUT INVENTION

Referring now to the drawings, a preferred embodiment of home traction device 10 is shown. Home traction device 10 generally has an elongated rectangular planar table 11 consisting of first rectangular cushion 12 and second rectangular cushion or vibrating pad 14. Both first and second rectangular cushions 12 and 14 are generally constructed having a rigid structural support means, such as plywood, supporting a cushion material, such as foam rubber, and covered with a suitable textile, such as naugahyde. Planar table 11 is supported by a first rectangular frame consisting of right side member 15, left side member 16, head end member 17, and foot end member 18. Longitudinal main brace 19 is attached to the underside of the first rectangular frame along its longitudinal centerline. T-shaped head leg member 20 is attached to the head end of longitudinal main brace 19 while T-shaped foot leg member 21 is attached to the foot end of longitudinal main brace 19. T-shaped foot leg member 21 is generally shorter in height, thereby disposing planar table 11 at a slight decline from its head to foot end.

A pelvic support frame 48 is attached approximately two-thirds of the way down first rectangular frame to longitudinal main brace 19 and right and left side members 15 and 16. Pelvic support frame 48 has a pair of pelvic uprights 49 supporting pelvic cross bar 50. Clamcleat 51 is centrally attached along pelvic cross bar 50. The details of clamcleat 51 are shown in FIG. *2a*. Clamcleats of this type are used in the rigging of sailboats and generally have a pulley aligned with a rope locking means, such as the angular ribs shown in FIG. *2b*.

Second rectangular cushion 14 is disposed within rectangular hole 13 in first rectangular cushion 12. Second rectangular cushion 14 is attached to second rectangular frame 23 which is in turn pivotally attached via vibrator springs 24 and elongated bolts 25 to cross braces 22. Cross braces 22 are transversely attached to longitudinal main brace 19. A vibrating motor 29, such as a Daton 3M564, is suspended from second rectangular frame 23 via motor mount 28. This particular configuration is shown in detail in FIG. 4.

Each vibrator spring 24 is provided with, at either end, a pair of crescent washers 26. Crescent washers 26 act to maintain springs 24 in a coaxial disposition about elongated bolts 25. Elongated bolts 25 and cooperating washers 27*a* and nuts 27*b* serve to pivotally attach second rectangular frame 23 to cross braces 22 through vibrator springs 24.

A weight brace extension 30 is perpendicularly attached to head end member 17. Weight brace extension 30 serves as a removable attachment point for angular weight brace 31. Angular weight brace 31, when engaged with weight brace extension 30, extends angularly upward from the head end of planar table 11. A weight pulley 32 is disposed in the extended most end of angular weight brace 31 for receiving nylon cord 34, or a similar flexible elongated member.

Nylon cord 34 serves as a tensive connector between water weight bag 33, or other adjustable weight means, and head harness 35. Head harness 35, which acts as a means for longitudinally supporting the head and suboccipital regions of patient 1, is attached to nylon cord 34 via head harness yoke 36. The details of head harness 35 are best shown in FIG. 5. Head harness 35 includes yoke attachment straps 37 having D-rings 38 for receiving head harness yoke 36. Yoke attachment straps 37 are attached to the main head harness member which includes cervical portion 39 and chin portion 40. A pair of harness adjustment straps 41 are adjustably attached between cervical and head portions 39 and 40 for securing head harness 35 about the head of patient 1.

The pelvis of patient 1 is elevated and longitudinally supported by pelvic harness 42, the details of which are shown in FIG. 6. Pelvic harness 42 generally has bell shaped main pelvic harness member 43 including multiple hook and latch attachment surfaces 45 for adjustably securing pelvic harness 42 about the pelvis of patient 1. Pelvic harness support strap 44 is attached to the apex of bell shaped main pelvic harness member 43 and has a D-ring 46 attached at its extreme end. D-ring 46 is provided to engage an S-hook 47 which in turn is connected to pelvic harness support rope 52.

In use, patient 1 secures pelvic harness 42 about his waist and pelvic area. The patient then attaches D-ring 46 to S-hook 47 which is suspended from clamcleat 51 via pelvic harness support rope 52. The effective length of pelvic harness support rope 52 can be adjusted accordingly to elevate the pelvis of patient 1 to the desired level. Head harness 35, already being attached to water weight bag 33, is then pulled over the head of patient 1. Patient 1 then secures harness adjustment straps 41 between the cervical and chin portions 39 and 40. Vibrator motor 29 is then activated and induces a relaxing vibration to the spinal area of the patient which is directed normal to planar table 11. Angular weight brace 31 and weight brace pulley 32 serve to convert the downward force of gravity on water weight bag 33 to a tensive force directed along the spine of patient 1, thereby producing the desired traction effect.

While there is shown and described the present preferred embodiment of the invention, it is to be distinctly understood that this invention is not limited thereto but may be variously embodied to practice within the scope of the following claims.

I claim:

1. A home traction device which comprises:

base means;

planar table means being attached to and supported by said base means;

pelvic support means for elevating and longitudinally supporting the pelvic area of a user;

head harness means for longitudinally supporting the head and suboccipital regions of a user;

tensive means cooperating with said pelvic support means and said head harness means for applying tensive forces to the spine of a user; and vibration means being disposed in said planar table means to induce vibrations normal to the plane of the table along the spine of the user.

2. The home traction device of claim No. 1 wherein said base means comprises:

a first rectangular frame having two parallel side members defining an elongated longitudinal dimension and two parallel end members defining a head end and a foot end;

a longitudinal main brace being attached to said frame in parallel spaced relation to said side members and being disposed centrally therebetween; and a plurality of leg members being attached to said frame for supporting the same in a generally horizontal position.

3. The home traction device of claim No. 2 wherein said planar table means comprises:

a first elongated rectangular cushion having rigid structural support means incorporated therein; and said cushion having an elongated rectangular hole therein, being disposed to juxtapose the spine of a user.

4. The home traction device of claim No. 3 wherein said vibration means comprises:

a vibrator frame pivotally attached to said longitudinal main brace;

a vibrating motor attached to said vibrator frame for imparting vibrations thereto; and a second generally elongated rectangular cushion having rigid structural support means therein and being attached to said vibrator frame, said second cushion further being disposed within the rectangular hole in said first cushion.

5. The home traction device of claim No. 4 wherein said pelvic support means comprises:

a pelvic frame being attached to said rectangular frame and having an attachment point disposed at an elevated position above the pelvic region of a user for adjustable attachment of a pelvic harness; and a pelvic harness adapted to securely receive the pelvic region of a user and being removably attached to said pelvic frame.

6. The home traction device of claim No. 5 wherein said tensive means comprises:

an adjustable weight means;

a flexible elongated member having a first end attached to said head harness means and a second end attached to said adjustable weight means; and a weight brace attached to said rectangular frame at the head end and disposed to slidably receive said flexible elongated member for connecting a downward tensive force to a longitudinal tensive force.

* * * * *